(12) United States Patent
Ayer et al.

(10) Patent No.: US 11,684,376 B2
(45) Date of Patent: Jun. 27, 2023

(54) SYSTEM AND METHOD FOR INTEGRATED SURGICAL GUIDE-HUB AND DRILL WITH GUIDED DRILLING AND PLUNGE PROTECTION

(71) Applicant: Hubly Inc., Wilmington, DE (US)

(72) Inventors: Amit Bhasker Ayer, Chicago, IL (US); Nathanael David Andrews, Palo Alto, CA (US); Casey Mimi Grage, Vienna, VA (US); Nisar Hemant Parekh, McKinney, TX (US)

(73) Assignee: HUBLY INC., Wilmington, DE (US)

( * ) Notice: Subject to any disclaimer, the term of this patent is extended or adjusted under 35 U.S.C. 154(b) by 70 days.

(21) Appl. No.: 17/061,040

(22) Filed: Oct. 1, 2020

(65) Prior Publication Data
US 2021/0085342 A1  Mar. 25, 2021

Related U.S. Application Data

(63) Continuation of application No. PCT/US2019/063820, filed on Nov. 28, 2019.
(Continued)

(51) Int. Cl.
*A61B 17/16* (2006.01)
*A61B 90/00* (2016.01)
(Continued)

(52) U.S. Cl.
CPC ...... *A61B 17/1695* (2013.01); *A61B 17/1628* (2013.01); *A61B 17/1739* (2013.01);
(Continued)

(58) Field of Classification Search
CPC . A61B 17/1695; A61B 90/03; A61B 17/1628; A61B 17/1739; A61B 2090/033; A61B 2017/00292
See application file for complete search history.

(56) References Cited

U.S. PATENT DOCUMENTS 3,515,100 A * 6/1970 Keller ................ A61B 17/1695
408/14
3,833,313 A * 9/1974 Gallion ................ B25H 1/0078
408/112
(Continued)

FOREIGN PATENT DOCUMENTS

JP   2001212158 A   8/2001
JP   2010082448 A   4/2010
(Continued)

OTHER PUBLICATIONS

Biotex Inc., "Phasor Drill," https://www.biotexmedical.com/case-studies-phasor/, 13 pages.
(Continued)

*Primary Examiner* — Kevin T Truong
*Assistant Examiner* — Diana Jones
(74) *Attorney, Agent, or Firm* — Slater Matsil, LLP

(57) ABSTRACT

A drilling system includes a guide-hub that includes contact feet configured to be placed against a drilling surface to maintain a fixed angle with the drilling surface. A drilling insert includes a drill bit and a harness. The drilling insert is configured to be inserted into the guide-hub and the harness is configured to detect when the drill bit punctures the drilling surface and automatically prevent further drilling.

20 Claims, 16 Drawing Sheets

Related U.S. Application Data

(60) Provisional application No. 62/773,036, filed on Nov. 29, 2018.

(51) Int. Cl.
    *A61B 17/17*           (2006.01)
    *A61B 17/00*           (2006.01)

(52) U.S. Cl.
    CPC .... *A61B 90/03* (2016.02); *A61B 2017/00292* (2013.01); *A61B 2090/033* (2016.02)

(56) References Cited

U.S. PATENT DOCUMENTS

| | | | |
|---|---|---|---|
| 5,133,720 A | | 7/1992 | Greenberg |
| 5,207,681 A | * | 5/1993 | Ghadjar .............. A61B 17/1695 606/180 |
| 5,993,453 A | | 11/1999 | Bullara et al. |
| 6,206,885 B1 | | 3/2001 | Ghahremani et al. |
| 6,228,088 B1 | | 5/2001 | Miller et al. |
| 6,622,731 B2 | | 9/2003 | Daniel et al. |
| 6,702,818 B2 | * | 3/2004 | Kupferschmid ... A61B 17/1695 606/80 |
| 6,749,574 B2 | | 6/2004 | Okeefe |
| 7,033,367 B2 | * | 4/2006 | Ghahremani ...... A61B 17/1695 606/108 |
| 7,780,679 B2 | | 8/2010 | Bobo, Sr. et al. |
| 7,981,122 B2 | * | 7/2011 | Labadie .............. A61B 17/1778 248/168 |
| 8,419,764 B2 | | 4/2013 | Begg |
| 8,747,418 B2 | * | 6/2014 | Qureshi .................. F16M 11/14 248/161 |
| 8,894,679 B2 | * | 11/2014 | Begg .................. A61B 17/3468 604/165.01 |
| 9,039,723 B2 | | 5/2015 | Begg |
| 9,387,313 B2 | | 7/2016 | Culbert et al. |
| 9,492,182 B2 | | 11/2016 | Keefer |
| 2010/0082035 A1 | | 4/2010 | Keefer |
| 2010/0298832 A1 | | 11/2010 | Lau et al. |
| 2012/0059378 A1 | * | 3/2012 | Farrell .................... A61B 90/25 606/80 |
| 2012/0203236 A1 | | 8/2012 | Mamourian |
| 2014/0094808 A1 | * | 4/2014 | Herndon ............ A61B 17/1695 606/80 |
| 2014/0288499 A1 | | 9/2014 | Miller |
| 2015/0031982 A1 | | 1/2015 | Piferi et al. |
| 2017/0150973 A1 | * | 6/2017 | Kwon ..................... A61B 17/17 |

FOREIGN PATENT DOCUMENTS

| | | |
|---|---|---|
| WO | 0061017 A1 | 10/2000 |
| WO | 2013029039 A1 | 2/2013 |
| WO | 2014176437 A3 | 10/2014 |
| WO | 2020113144 A1 | 6/2020 |

OTHER PUBLICATIONS

Novo Surgical, "Cushing Perforating Drill," http://novosurgical.com/cushing-perforating-drill.html, 3 pages.
Phasor Health, LLC., Phasor Cordless Drill, http://www.flasurgical.net/product-details/phasor-health/ 5 pages.
Phasor Health, LLC., Upgrade, https://www.phasorhealth.com/, 7 pages.
"Craniotomy," Johns Hopkins Medicine, retrieved, Nov. 1, 2017, 7 pages.
"Craniotomy," Mayfield Brain & Spine, MayfieldClinic.com, Apr. 2016, 5 pages.
"Emergency Department Visits, Hospitalizations and Deaths 2002-2006," Traumatic Brain Injury in the United States, www.cdc.gov/TraumaticBrainInjury, [no date], 74 pages.
"Guided, Perforating Bone Biopsy Kit with Drill," OmniBone, http://www.lauranemedical.com/LauraneUK/publicatoins/, [no date], 2017, 1 page.
"Our Latest Masterpiece Acra-Cut Smart Drill," Model 200-500 14/9mm SDR Smart Drill, [no date] 2003, 2 pages.
"Power Tools for Neurosurgery," Novag, v39/18, www.nouvag.com, [no date], 12 pages.
"The Electric Stealth-Midas MR8 System," Medtronic, www.medtronic.com, May 2019, 34 pages.
"The Midas Rex Microsaw and Triton System," Microsaws and Triton Electric High-Torque Handpiece, Medtronic, Fort Worth, Texas, www.medtronic.com, Feb. 2019, 20 pages.
Awad, et al., "Surgical Performance Determines Functional Outcome Benefit in the Minimally Invasive Surgery Plus Recombinant Tissue Plasminogen Activator for Intracerebral Hemorrhage Evacuation (MISTIE) Procedure," Research-Human-Clinical Trials, vol. 0, No. 0, Mar. 30, 2019, 12 pages.
Baum, et al., "External ventricular drain practice variations: results from a nationwide survey," J Neurosurg vol. 127: 1190-1197, Nov. 2017, 8 pages.
Cohen-Gadol, "External Ventricular Drain," The Neurosurgical Atlas, Nov. 10, 2017, 18 pages.
Couldwell, et al., "Computer-aided design/computer-aided manufacturing skull base drill," Neurosurgical Focus, vol. 42(5):E6, Accepted Feb. 24, 2017, 6 pages.
Edwards, "Cost-consequence analysis of antibiotic-impregnated shunts and external ventricular drains in hydrocephalus," J Neurosurg vol. 122: 139-147, Jan. 2015, 9 pages.
Eftekhar, "App-assisted external ventricular drain insertion," J Neurosurg 125:754-758, vol. 125, Sep. 2016, 5 pages.
Fried, et al., "The Insertion and Management of External Ventricular Drains: An Evidence-Based Consensus Statement," neurocritical care society, Springer Science+Business Media New York, Jan. 6, 2016, 21 pages.
Haidegger, et al., "Future Trends in Robotic Neurosurgery," NBC [no date] 2008, www.springerlink.com, Springer-Verlag Berlin Heidelberg 2008, 5 pages.
Hoffmann, "Phasor Drill," letter dated Dec. 1, 2016, 9 pages.
Ikeda, et al., "Cranionavigator Combining a High-speed Drill and a Navigation System for Skull Base Surgery," Neurol Med Chir (Tokyo) 39, 701-708, Accepted May 24, 1999, 8 pages.
Integra Limit Uncertainty, Integra Neurocritical care Product Catalogue, Europe, Middle-east and Africa only, [no date], 28 pages.
Integra, Cranial Access Kits, Neurocritical Care Solutions, [no date], 5 pages.
IQ Intelligent System, Usage Guidelines, Biomet Microfixation, One Surgeon. One Patient, [no date] 2 pages.
Jannetta, et al., "Epidemiology of ventriculostomy in the United States from 1997 to 2001," https://www.researchgate.net/publications/5504475, Article in British Journal of Neurosurgery, May 2008, 7 pages.
Loschak, et al., "Assured Safety Drill with Bl-Stable Bit Retraction Mechanism," Proceedings of the ASME 2013 International Design Engineering Technical Conferences & Computers and Information in Engineering Conference, Portland, Oregon, Aug. 4-7, 2013, 8 pages.
Loschak, et al., "Cranial Drilling Tool with Retracting Drill Bit Upon Skull Penetration," [no date], 1 page.
Manfield, et al., "Real-time ultrasound-guided external ventricular drain placement: technical note," Neurosurgical Focus, vol. 43 (5):E5, Submitted Mar. 9, 2017 Accepted Jul. 25, 2017, 5 pages.
PCT International Search Report and the Written Opinion of the International Searching Authority, PCT Application No. PCT/US2019/063820, dated Mar. 23, 2020, 14 pages.
Park, et al., "Accuracy and Safety of Bedside External Ventricular Drain Placement at Two Different Cranial Sites: Kocher's Point versus Forehead," J Korean Neurosurg Soc 50: 3-17-321, Aug. 8, 2011, 5 pages.
Rehman, et al., "A US-based survey on ventriculostomy practices," Clinical Neurology and Neurosurgery 114 (2012) 651-654, journal homepage: www.elsevier.com/locate/clineuro, Accepted Dec. 24, 2011, 4 pages.
Rosenbaum, et al., "Ventriculostomy: Frequency, length of stay and in-hospital mortality in the United States of America, 1988-2010,"

(56) References Cited

OTHER PUBLICATIONS

Journal of Clinical Neuroscience 21 (2014) 623-632, journal homepage: www.elsevier.com/locate/jocn, Accepted Sep. 12, 2013, 10 pages.
Stryker, Neuro Spine ENT, Improved Maestro Drill, access to better Outcomes, www.stryker.com, [no date], 2 pages.
Stryker, Neuro, Spine, ENT, Maestro Pneumatic Drill, www.stryker.com, [no date], 2 pages.
Stryker, S2, Specialty Inspired Innovation, Precision Defined, 2012, 4 pages.
Communication pursant to Rule 164(1) EPC, European Application No. 19888688.9, dated Jun. 24, 2022, 10 pages.
Extended European Search Report, European Application No. 19888688.9, dated Sep. 26, 2022, 9 pages.

* cited by examiner

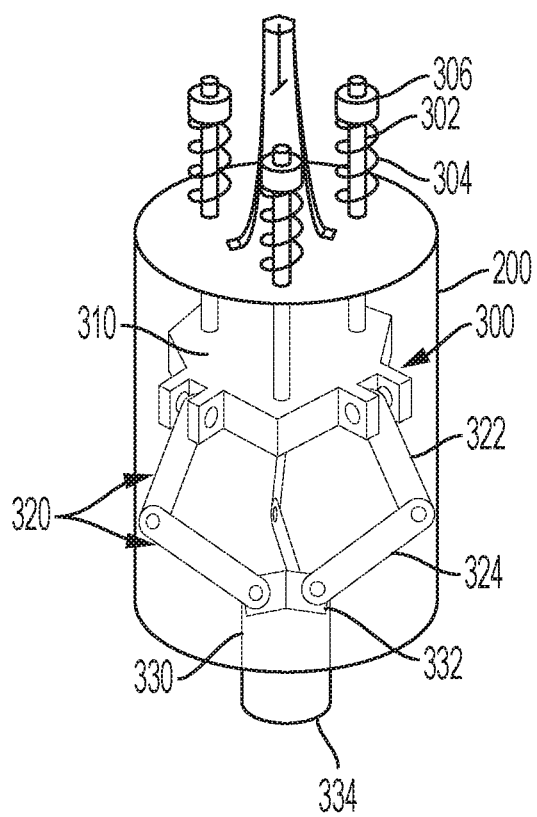
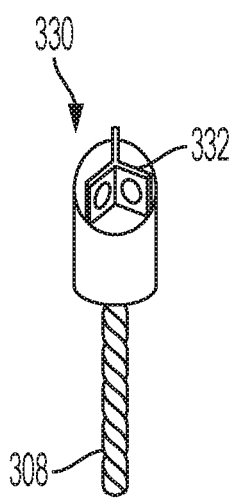
FIG. 4A
FIG. 4B

SYSTEM AND METHOD FOR INTEGRATED SURGICAL GUIDE-HUB AND DRILL WITH GUIDED DRILLING AND PLUNGE PROTECTION

CROSS-REFERENCE TO RELATED APPLICATIONS

This application is a continuation application of International Application No. PCT/US2019/063820, filed on Nov. 28, 2019, which claims the benefit of U.S. Provisional Application No. 62/773,036, filed on Nov. 29, 2018, which applications are hereby incorporated herein by reference.

TECHNICAL FIELD

The present invention relates to an integrated surgical guide-hub and drill with guided drilling and plunge protection, and in particular embodiments, integrated component system with a guide-hub, scalp retraction mechanisms, hemostasis mechanisms, catheter guide compatible with a guide-hub, augmented reality tracking and integration, positioning sensors, and tunneling compatible guide-hub.

BACKGROUND

Many medical conditions require access to the brain for the purpose of placing a catheter or electrode. For example, hydrocephalus is a condition where cerebrospinal fluid accumulates in the brain and may lead to a life-threatening pressure increase in the brain. Placement of an external ventricular drain (EVD) is a typical treatment for hydrocephalus. In order to place an EVD, a drill is used to penetrate the skull and a catheter is inserted into to the ventricle in the brain. The drill commonly used today is a hand-crank drill that is guided and controlled by a neurosurgeon's skill and feel. The current procedure is complication prone and often results in a misplaced catheter. A misplaced catheter is ineffective for the EVD, introduces the potential for infection, and may independently cause physical damage to the brain.

There is another device, the Ghajar Guide, that adds components to improve the EVD procedure, but it is only used by a small minority of neurosurgeons due to the additional complexity, components, and steps involved. The Ghajar Guide is not used in the majority of all procedures because surgeons often find it adds complexity and additional steps to the surgery and increases cost.

SUMMARY

In accordance with an embodiment of the present application, a drilling system that includes a guide-hub that includes contact fee and a drilling insert that includes a drill bit and a harness. The contact feet are configured to be placed against a drilling surface to maintain a fixed angle with the drilling surface. The drilling insert is configured to be inserted into the guide-hub and the harness is configured to detect when the drill bit punctures the drilling surface and automatically prevent further drilling.

In accordance with another embodiment of the present application, a drilling system that includes a guide-hub and a drilling insert. The guide-hub includes an upper cylindrical portion and a lower cylindrical portion. The upper cylindrical portion and the lower cylindrical portion having two diameters. The drilling insert includes a harness portion and a drilling portion. The harness portion rotates within the upper cylindrical portion and the drilling portion rotates within the lower cylindrical portion.

In accordance to another embodiment of the present application, a medical tool that includes a cranial access drill. The cranial access drill includes a motor, a guide-hub, a mechanical harness, a drill shaft, and angle alignment feet. The guide-hub includes a retraction portion, a guide portion, and an alignment portion. The mechanical harness rotates inside the retraction portion, and the drill shaft rotates inside the guide portion. The angle alignment feet are coupled to the guide-hub at the alignment portion, and the angle alignment feet maintain an angle of alignment between a drilling surface and the cranial access drill.

In accordance to another embodiment of the present application, a method of using a drilling system includes placing a guide-hub that on a drilling surface, guiding a drilling insert that includes a drill bit and a harness into the guide-hub, drilling the drilling surface with the drill bit, detecting when the drill bit punctures the drilling surface using the harness, and automatically stopping the drilling in response to detecting that the drill bit has punctured the drilling surface. The guide-hub includes an axial direction and the axial direction of the guide-hub is parallel to a surface normal of the drilling surface during drilling.

BRIEF DESCRIPTION OF THE DRAWINGS

For a more complete understanding of the present invention, and the advantages thereof, reference is now made to the following descriptions taken in conjunction with the accompanying drawings, in which:

FIGS. 4A and 4B illustrates a perspective view of an embodiment of a drilling structure;

DETAILED DESCRIPTION OF ILLUSTRATIVE EMBODIMENTS

Figures 1A, 1B, 1C, 1D:
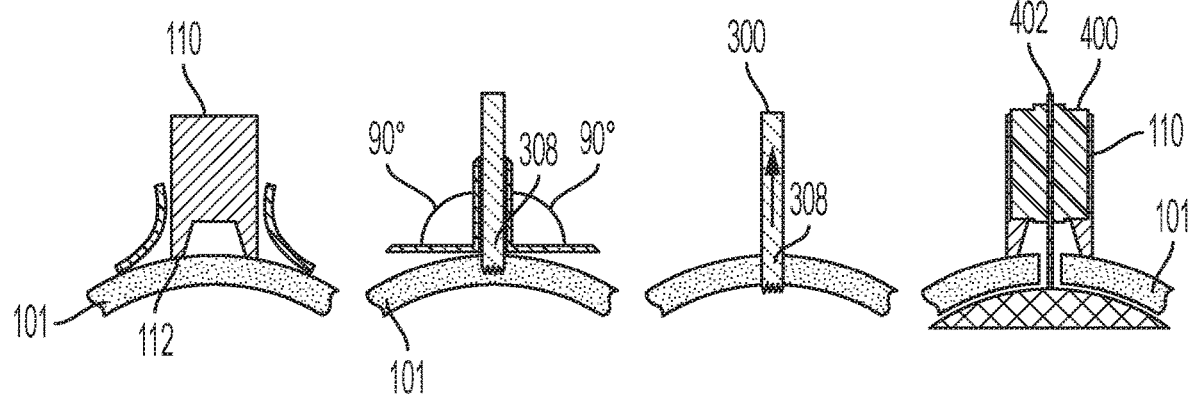
FIGS. 1A-1D illustrate a high-level sequence of a surgical process in various embodiments.

Currently, the procedure for placing an external ventricular drain (EVD), a life-saving device for removing excess fluid from the brain, uses a hand-powered crank drill to drill through the skull and place a catheter in the ventricle of the brain. The most commonly used hand-crank drill provides no protection for preventing misplacement or plunge. Instead, the hand-powered crank drill relies on neurosurgeon skill and feel. The commonly used hand-crank drill has several problems. Particularly, the commonly used crank drill is hand-powered, has no mechanism to prevent plunging into the brain after puncturing the skull during drilling, has no alignment guide to ensure the proper drilling angle, includes too many components leading to unnecessary complexity, does not include scalp retraction, and does not include any hemostasis mechanism.

As a result of these device shortcomings, the current procedures that use the existing hand-powered crank drill exhibit higher complication rates due to catheter misplacement or other surgeon errors (including plunge). During drilling, the drill is prone to shift drilling angle. Maintaining a perpendicular drilling angle is important for properly placing the catheter in the correct position. Further, maintaining a perpendicular catheter insertion trajectory is also important for properly placing the catheter. Thus, both misaligned holes formed by misaligned drilling and misaligned catheter insertion trajectory can lead to misplacement of the catheter.

Another problem that can arise during drilling occurs as the drill penetrates the skull. If the neurosurgeon applies too much pressure while drilling and does not detect that he or she is about to penetrate the skull, the neurosurgeon may plunge the drill bit into the brain. This type of plunge can result in severe injury, complication, or death.

Various embodiments described herein reduce or prevent catheter misplacement and drill plunge. Both problems, misplacement and plunge, cause substantial complications leading to poor outcomes for patients and increased costs for hospitals. Various embodiments include a guide-hub that maintains both the perpendicular drilling angle and the perpendicular catheter insertion trajectory. Some embodiments also include an automatic plunge protection mechanism (or a harness in multiple embodiments) that withdraws the drill bit automatically as the drill bit penetrates the skull. In addition to these primary problems, various embodiments provide an integrated solution that brings together a complete guide-hub and drill system with other solution elements, including one or more of (1) an electric drill, (2) integrated component system with the guide-hub, (3) a scalp retraction mechanism, (4) a hemostasis mechanism, (5) a catheter guide compatible with the guide-hub, (6) augmented reality tracking and integration for further reducing misplacements, (7) positioning sensors for further reducing misplacements, and (8) a tunneling compatible guide-hub.

In various embodiments, our solution seeks to provide a modern surgical drill that addresses multiple problems in an easy-to-use integrated hub-drill system. Particularly, embodiments include some or all of the following features: (1) reduction of catheter misplacements with a drill guide-hub that maintains drill position and orientation; (2) prevention of plunge with an automatic drill bit plunge protection mechanism; (3) improvement of surgeon efficiency, speed, endurance, and accuracy with an electric power drive system; (4) improvement of surgeon usability (increasing efficiency, speed, and accuracy) with an integrated surgical guide-hub and drill system; (5) improvement of integration with a scalp retraction mechanism integrated directly in the guide-hub; (6) prevention of excessive bleeding, infection, and complications with a hemostasis mechanism; (7) further reduction of catheter misplacements with a catheter guide compatible with the guide-hub; (8) further reduction of catheter misplacements with an augmented reality tracking and integration system; (8) further reduction of catheter misplacements with positioning sensors; and (9) further simplification of surgical procedures with a tunneling compatible guide-hub.

In order to achieve some of these features, various embodiments include precise dimensions. Some embodiments include materials with appropriate coefficients of static friction to enable a friction holding position during drilling that automatically releases after drilling through a hard surface so that automatic drill bit retraction is enabled. Some of these embodiments also include springs for the automatic drill bit retraction with proper spring constants to enable the friction holding position during drilling and the automatic drill bit retraction once puncture occurs. Various embodiment also include one or more of (1) an electric drill, (2) an integrated component system with the guide-hub, (3) a scalp retraction mechanism, (4) a hemostasis mechanism, (5) a catheter guide compatible with the guide-hub, (6) augmented reality tracking and integration for reducing misplacements, (7) positioning sensors for reducing misplacements, and (8) a tunneling compatible guide-hub.

Production of various embodiments can be accomplished in several ways. In a first instance, the parts can be machined by a machinist and assembled into the system. In another instance, the system can be manufactured in an industrial manufacturing process that may include automated assembly, forming or casting components, and any other industrial manufacturing processes. In a further instance, the system can be produced using advanced manufacturing tools such as a 3D printer or computer numerical control (CNC) machines, for example. In short, embodiments can be produced using several techniques known to those of skill in the art. The selection of processes and materials is informed by addressing the issues of biocompatibility, durability, and cost according to embodiments described herein.

Some embodiments are used as a drill to penetrate the skull during surgery. A common procedure that requires a drill for the skull is placement of an EVD, which includes placing a catheter into the brain. An embodiment would be used in such a procedure. The guide-hub would be placed against the skull after the skin is retracted, which may be accomplished through the integrated scalp retraction mechanism. The drill would be guided through the guide-hub to penetrate the skull. Immediately after penetrating the skull, the plunge protection mechanism or harness would prevent the drill bit from plunging into the brain. Then, the drill is removed from the guide-hub and a catheter guide is used with the guide-hub to maintain the position and alignment of the catheter as it is inserted into the brain. Other features or components of the solution may be used along with this process as described further herein.

A schematic embodiment of a method of a surgical process will be first described using FIGS. 1A-1D and a detailed embodiment of a method of a surgical process will be described using FIGS. 2A-2D. A detailed embodiment of a drilling structure will be described using FIG. 3 and alterative embodiments of a drilling structure will be described using FIGS. 4, 13 and 14. An embodiment of a guide hub will be described using FIG. 5, alternative embodiments of a guide-hub will be described using FIGS. 7A-7B, 8A-8D, 10, and 11A-11D, and a schematic embodiment of a method of using an alternative guide-hub using FIG. 12A-12D. An embodiment of a catheter guide will be described using FIG. 6. A detailed embodiment of a scalp retractor will be described using FIGS. 9A-9D. A detailed embodiment of a plunge protection harness will be described using FIG. 15.

FIGS. 1A, 1B, 1C, and 1D illustrate a high-level sequence of a surgical process in various embodiments. In FIG. 1A, the scalp is opened and a guide-hub 110 is placed on a skull 101. The support legs 112 of the guide-hub 110 are placed against the skull 101 and maintain a perpendicular alignment. In FIG. 1B, a drill bit 308 supported by a central drill shell 200 is aligned inside the guide-hub 110 and drilling is performed with perpendicularity maintained by the guide-hub 110. The guide-hub 110 is omitted from FIG. 1B for simplicity of illustration. In FIG. 1C, as a drill bit 308 penetrates the skull 101, a plunge protection harness 300 detects when the drill bit 308 punctures the skull 101 and retracts the drill bit 308 automatically or prevents further plunge. The plunge protection harness 300 is omitted from FIG. 1C for simplicity of illustration. In FIG. 1D, a catheter guide 400 is inserted inside the guide-hub 110 and used to guide the catheter 402 for accurate placement. The guide-hub 110 maintains the perpendicular alignment of the catheter guide 400, which ensures perpendicular catheter trajectory and reduced misplacement of the catheter 402.

Figure 2A:
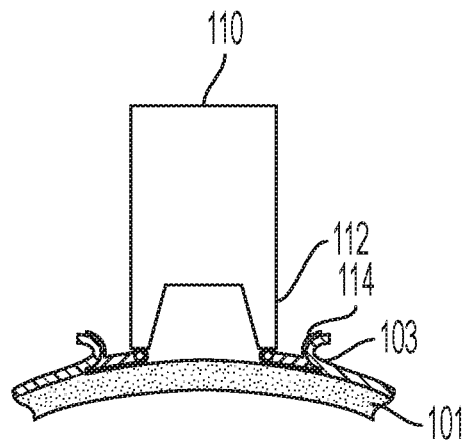
FIGS. 2A-2D illustrate a detailed sequence of the surgical process in FIGS. 1A-1D.

FIGS. 2A, 2B, 2C, and 2D illustrate each of the four steps of FIGS. 1A, 1B, 1C, and 1D in detail. FIG. 2A illustrates accessing a skull 101, where a guide-hub no is placed against the skull 101 after an incision is made in the scalp 103. The guide-hub no includes support legs 112 for contacting the skull 101 (contact feet) and scalp retractors 114 extending from the support legs as feet extensions for holding back the scalp 103. The scalp retractors 114 include a homeostasis mechanism to reduce bleeding from the scalp. One example of the homeostasis mechanism is pressure clips that apply clamping pressure on the scalp. In alternative embodiments, the scalp retractors or homeostasis mechanism are omitted.

Figure 2B:
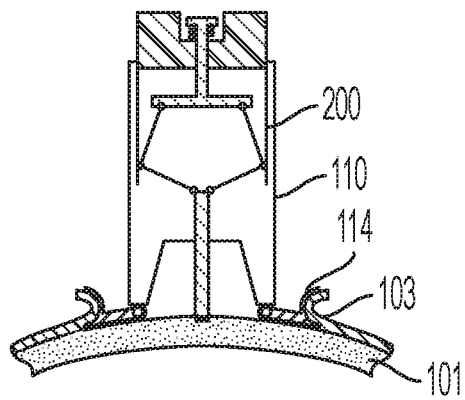

FIG. 2B illustrates aligning the drill 202 and drilling through the skull 101. The guide-hub 110 maintains the perpendicularity with the skull 101 while the drill 202 is guided through the guide-hub 110. The central drill shell 200 spins inside the guide-hub 110. A motor or drill drives the rotation of the central drill shell 200. The drill or motor is omitted from this illustration for simplicity.

Figure 2C:
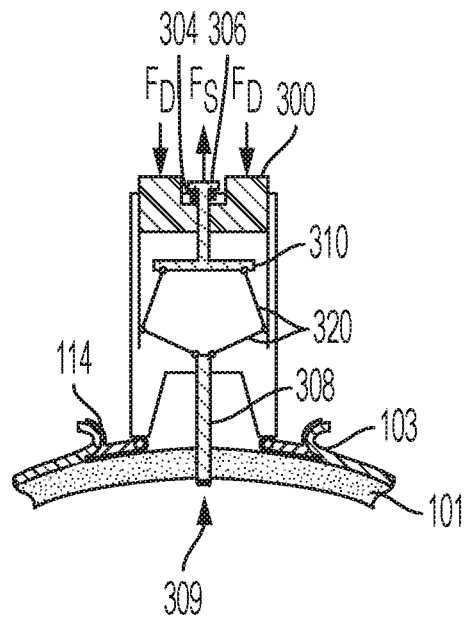

FIG. 2C illustrates a plunge protection harness 300. Before pressing the drill bit tip 309 against the skull 101, a joint shoulder 310 is depressed. The joint shoulder 310 support joint arms 320, passes through the central drill shell 200, and is in contact with a spring 304. Depressing the joint shoulder 310 compresses the spring 304 and extends the drill bit 308 supported by the joint arms 320 downwards. As the drill bit tip 309 is in contact with the skull 101 and pressure is applied, the joint arms 320 supporting the drill bit 308 expand outward and lock into position on the internal wall of the central drill shell 200 due to friction. The lock with the internal wall due to friction prevents the spring 304 from returning the joint shoulder 310 to its neutral position. As long as the pressure is maintained, the friction between the internal wall of the central drill shell 200 and the supporting joint arms 320 prevents the spring force Fs from retracting the joint shoulder 310, joint arms 320, and drill bit 308. As soon as the drill bit 308 penetrates the skull 101, the counteracting force on the drill bit tip 309 ceases. Because the force on the drill bit tip 309 disappears, the horizontal forces maintaining the lock due to friction between the joint arms 320 and the internal wall of the central drill shell 200 is lost. Thus, the spring force Fs will automatically withdraw the joint shoulder 310, joint arms 320, and drill bit 308 once skull penetration is achieved.

According to various embodiments, in order to allow the spring force Fs to withdraw the joint shoulder 310, joint arms 320, and drill bit 308 immediately upon penetrating the skull 101, the force downward driving the drill pressure, the drill force $F_D$, is applied to the central drill shell 200 but not to the joint shoulder 310 and spring 304. As shown in FIG. 2C, the drill force $F_D$ is applied to the central drill shell 200 but not to the joint shoulder 310 connected to the joint arms 320. In this way, the drill force $F_D$ is transmitted to the drill bit 308 through the central drill shell 200, the lock caused by friction, and the lower joint arms 324. Thus, as soon as the lock caused by friction between the joint arms 320 and the internal wall of the central drill shell 200 is released, the drill force $F_D$ is decoupled from the drill bit 308.

Figure 2D:
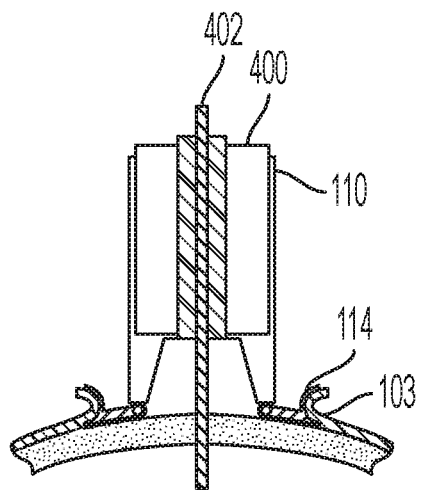

FIG. 2D illustrates guiding the catheter trajectory with a catheter guide 400 that is inserted into the guide-hub 110 once the central drill shell 200 (not shown in FIG. 2D) is removed. After penetrating the skull 101, the central drill shell 200 (not shown in FIG. 2D) with the plunge protection harness 300 and drill bit 308 are removed from the guide-hub 110. In place of the central drill shell 200, the catheter guide 400 is inserted into the guide-hub 110. The catheter guide 400 maintains the perpendicularity of a catheter 402 during insertion by referencing the alignment of the guide-hub 110 that is maintained by the support legs 112 set against the skull 101. Using this solution, the perpendicularity of the drilling and the catheter placement is improved. Further, the plunge protection harness 300 prevents injury, complication, and death from over-drilling and plunging of the drill bit 308. The scalp retractors 114 integrated into the guide-hub 110 simplify the surgical sequence and maintain component alignment and integrity. The homeostasis mechanism reduces bleeding to further prevent complications. In other embodiments, the catheter guide 400 is integrated into the guide-hub 110 such that there is not a separate insertion step of the catheter guide.

Figure 3:
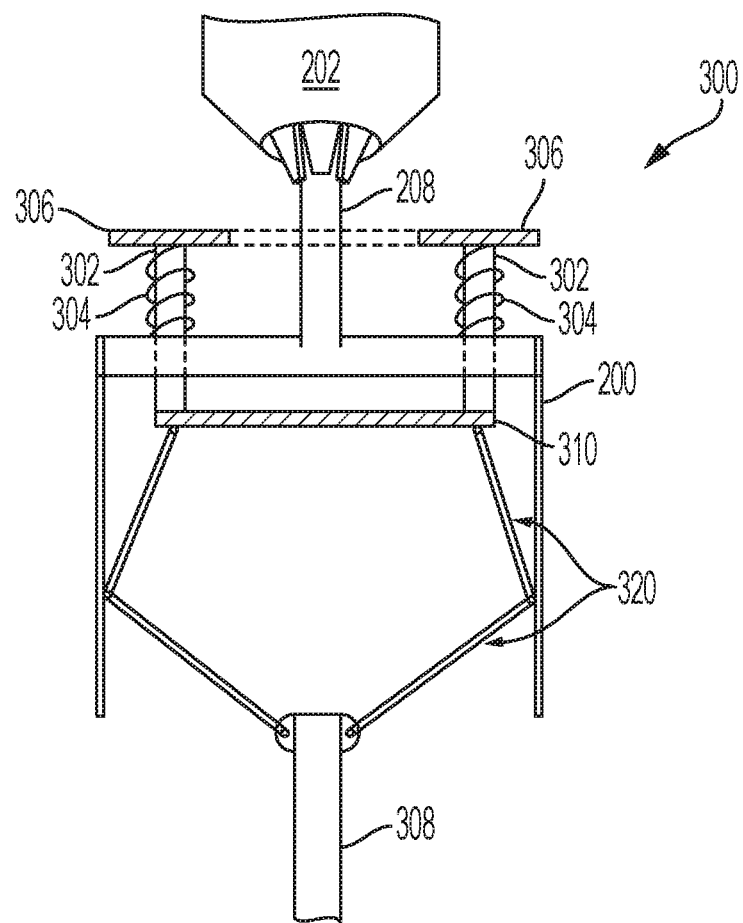
FIG. 3 illustrates a cross-sectional view of one embodiment of a drilling structure.

FIG. 3 illustrates a zoomed in cut-away of a drilling structure 100 which includes a central drill shell 200 and a plunge protection harness 300 within the central drill shell 200 as described in reference to FIGS. 2A, 2B, 2C, and 2D, but FIG. 3 includes more detail and a different arrangement of some portions. The joint shoulder 310 still supports the joint arms 320, which support the drill bit 308. However, the joint shoulder 310 is coupled to two support shafts 302 that each have a restoring spring 304 in this instance. With this configuration, the drill 202 can drive a central drive shaft 208 that supports and drives the central drill shell 200.

FIG. 4A illustrates a perspective view of a more detailed drilling structure 100 which includes the central drill shell 200 and the plunge protection harness 300 as described in reference to FIGS. 2A, 2B, 2C, 2D, and 3, but FIG. 4A includes more detail and a different arrangement of some portions according to various embodiments. As shown, the joint shoulder 310 is a 3D piece that includes and supports three sets of joint arms 320 extending to a drill bit structure 330. Each of the joint arms 320 includes a lower joint arm 324 and an upper joint arm 322. The drill bit structure 330 may include a joint receiver portion 332 and an insert portion 334 for attaching a drill bit 308 (which could be threaded, for example). In FIG. 4B, the drill bit structure 330 may be a single fabricated piece with the joint receiver portion 332 integrated with the drill bit 308. In some particular embodiments, the single fabricated piece includes the drill bit 308 embedded into the joint receiver 332 as a unitary piece.

The central drill shell 200 is a cylinder with a top surface that has three holes for extending support shafts 302 through the holes to the joint shoulder 310. The three support shafts 302 each have stoppers 306 that couple a spring 304 to the shaft and lock the three springs 304 on the three support shafts 302 between the stoppers 306 and the top surface of the central drill shell 200. The support shafts 302 extend to and support the joint shoulder 310. The top surface of the central drill shell 200 also includes a central drive shaft 208 extending upward. The central drive shaft 208 is connected to a drill drive, such as an electric drill motor, or another motor that causes the central drill shell 200 to spin. A hand powered drill drive is used in alternative embodiments. The central drive shaft 208 may have a hexagonal cross-section, as shown, or other shapes for coupling to the drill drive.

As described further hereinabove, the joint arms 320 extend outward and lock into place, with a friction lock, against the internal wall of the central drill shell 200 when the drill bit 308 is pressed against the skull 101 during drilling. Thus, the drill force $F_D$ applied to the central drive shaft 208 by the drill drive is transmitted to the drill bit 308 through the central drill shell 200 wall, the friction lock, and the lower joint arms 324 that are connected to the joint receiver portion 332 of the drill bit structure 330.

Figure 5:
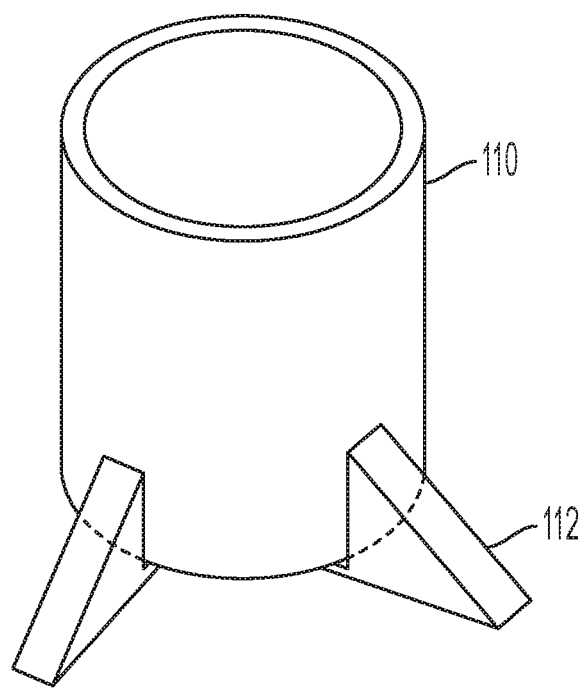
FIG. 5 illustrates a perspective view of one embodiment of a guide-hub.

FIG. 5 illustrates a perspective view of a guide-hub 110 showing additional detail and a different arrangement of some portions. The guide-hub 110 is set against the skull 101 and maintains perpendicularity with the skull 101 as described hereinabove in reference to FIGS. 1A, 1B, 1C, 1D, 2A, 2B, 2C, and 2D. The guide-hub 110 receives a central drill shell 200 and maintains perpendicularity of the central drill shell 200 and drill bit 308 during drilling. After the drill bit 308 penetrates the skull 101 and drilling is complete, the guide-hub 110 receives a catheter guide 400 and maintains perpendicularity of the catheter trajectory during catheter placement. In other embodiments, the guide-hub 110 includes an integrated catheter guide 400 that is not removed during drilling and is used after drilling to guide the catheter 402 into place. The guide-hub 110 may also include additional attachments as described further herein, but those attachments are omitted from FIG. 5 for simplicity of illustration.

Figure 6:
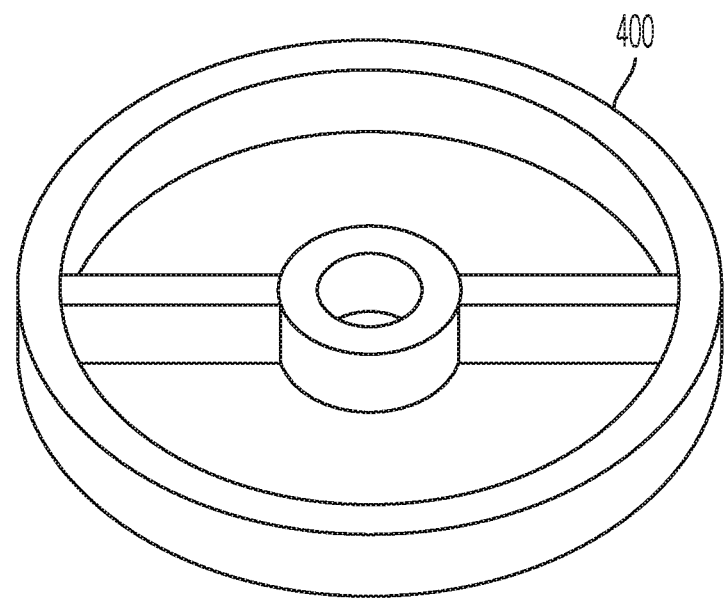
FIG. 6 illustrates a perspective view of one embodiment of a catheter guide.

FIG. 6 illustrates a perspective view of a catheter guide 400. In some embodiments, the catheter guide 400 is inserted into the guide-hub 110 after the central drill shell 200 is removed. The catheter guide 400 conveys the perpendicular alignment reference of the guide-hub 110 to the catheter 402 and maintains the perpendicularity of the catheter 402 during insertion. By maintaining a perpendicular trajectory during catheter insertion, catheter misplacement is prevented, avoiding complications such as ineffective treatment and infection, for example. The catheter guide 400 may be similar in height to the guide-hub 110 (as shown in FIG. 2D) or may have a much lower profile as shown here in FIG. 6. In another instance of our solution the catheter guide 400 includes a depth gauge for further improving placement accuracy.

Figure 7A:
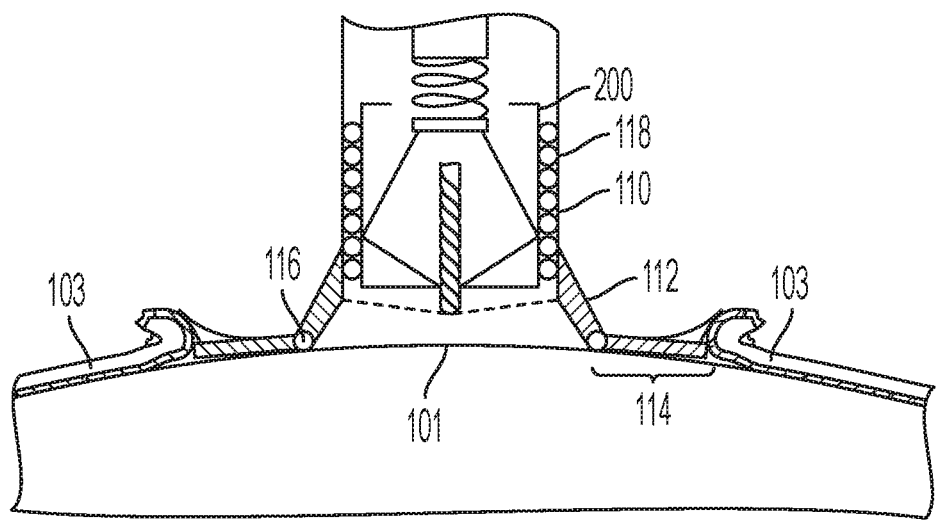
FIG. 7A illustrates a cross-sectional view of one embodiment of a guide-hub, support legs, and scalp retractors.
Figure 7B:
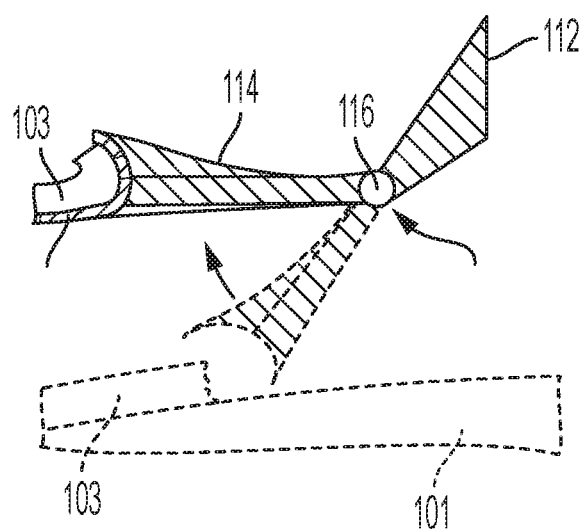
FIG. 7B illustrates a magnified view of the support legs and scalp retractors of the embodiment in FIG. 7A.

FIGS. 7A and 7B illustrate a cross-sectional and expanded view of support legs 112 and scalp retractors 114 according to some embodiments. In such embodiments, the support legs 112 set against the skull 101 and include scalp retractors 114 on hinges at the ends of the support legs 112. As the support legs 112 are placed on the skull 101, the scalp retractors 114 catch the scalp 103 and other tissues, such as the periosteum membrane, and hold the scalp 103 away from the drilling location. This additional solution also may include ball bearings 118 between the guide-hub no and the central drill shell 200 as shown. In some embodiments, the joint 116 in the support legs 112 (contact feet) connecting the support legs 112 to the scalp retractors 114 (feet extensions) may be a joint or hinge that has high friction or may be a spring joint as shown in FIG. 7B. In other embodiments, the hinge may have less friction or be another type of joint or hinge.

Figure 8A:
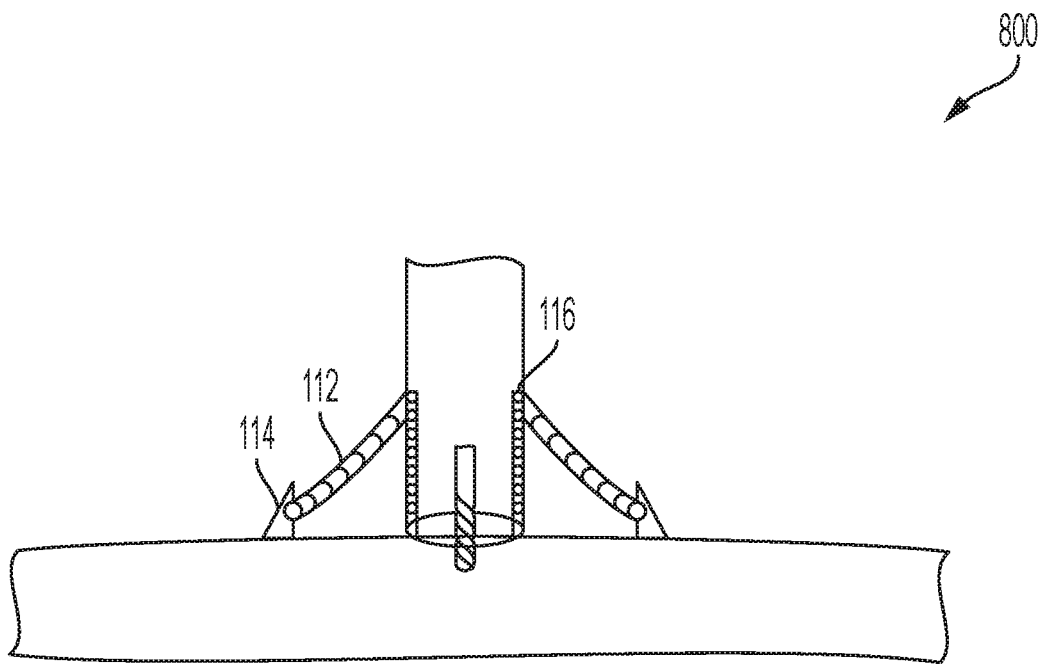
FIG. 8A illustrates a side view of one embodiment of a guide-hub, guide-hub support legs, and scalp retractors.
Figure 8B:
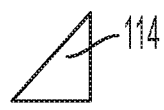
FIGS. 8B-8D illustrates various embodiments of the scalp retractors in FIG. 8A.
Figure 8C:
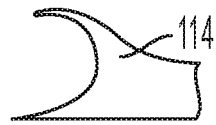
Figure 8D:
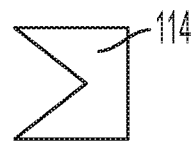

FIG. 8A illustrates a side view of support legs 112 according to another embodiment. The support legs 112 are attached to the guide-hub 110 as described herein, but in this embodiment, the support legs 112 are made of a resilient material or structure. Thus, the support legs 112 expand outward as the guide-hub 110 is pressed against the skull 101. FIGS. 8B, 8C, and 8D also illustrate alternative scalp retractor 114 pieces for attachment to the end of the support legs 112.

Figure 9A:
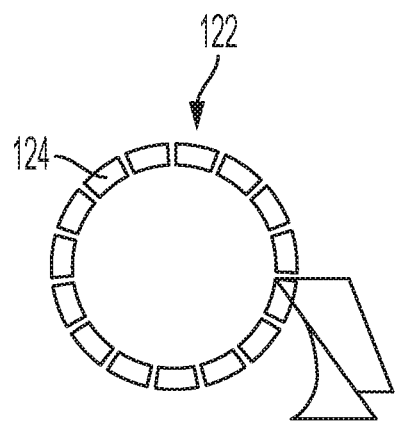
FIGS. 9A-9D illustrate multiple view of one embodiment of a scalp retraction mechanism.
Figure 9B:
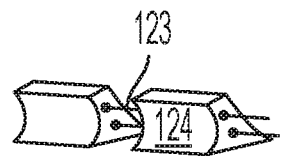
Figure 9C:
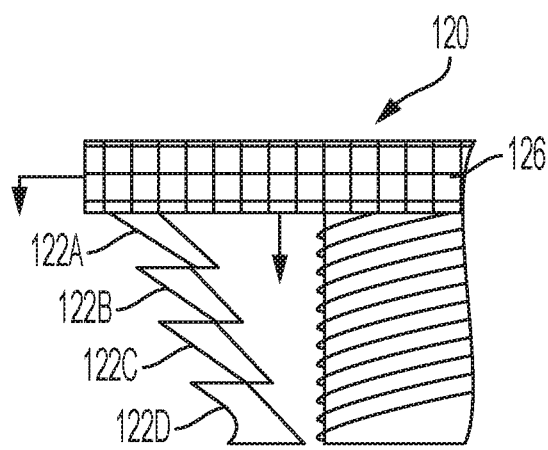
Figure 9D:
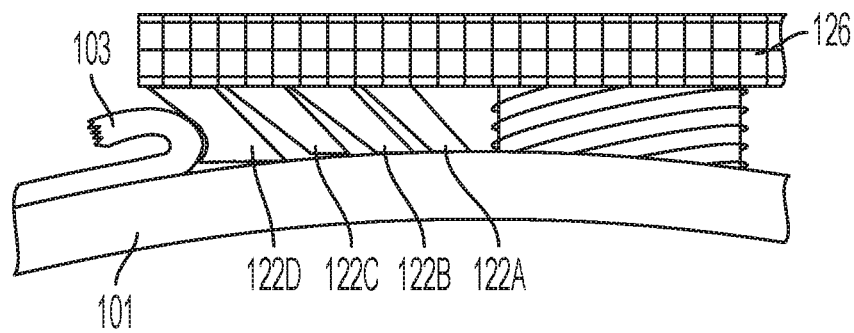

FIGS. 9A, 9B, 9C, and 9D illustrate a scalp retractor 114 according to another embodiment. FIG. 9A illustrates a top view of an interlocking ring 122 and its spacers 124. FIG. 9B illustrates a perspective view of spacers 124 connected by stretchable or elastic materials 123 of an interlocking ring 122. FIG. 9C illustrates a front view of the scalp retractor 114 which is provided by a series of interlocking rings 122 around a guide-hub 110. As the interlocking rings 122 are pushed downward, each interlocking ring 122 slides inside the interlocking ring 122 below it and forces the ring below it to expand outward, which in turn forces the ring below that ring to also expand outward and so on. In this embodiment, the first interlocking ring 122A pushes the second interlocking ring 122B down, which pushes the third interlocking ring 122C down, which pushes the fourth interlocking ring 122D. As the fourth interlocking ring 122D is pushed, it expands outward along the skull 101 and retracts the scalp 103. FIG. 9D illustrates a front view of a compressed scalp retractor 114 of FIG. 9C. The rings are pushed down by a structure that can slide downwards and can be locked in place by applying a force to the topmost interlocking ring 122. In the solution illustrated in FIGS. 9C-9D, the structure is a large ring 126 that twists on threading on the outside of the guide-hub 110.

The number of interlocking rings 122, illustrated as four, may be larger or smaller in different solution instances. The interlocking rings 122 are expandable. As shown in FIGS. 9A and 9B, the rings are connected by a stretchable or elastic material 123. In another solution, the interlocking rings could use an expandable sliding ring structure that is not elastic but is capable of expansion.

Figure 10:
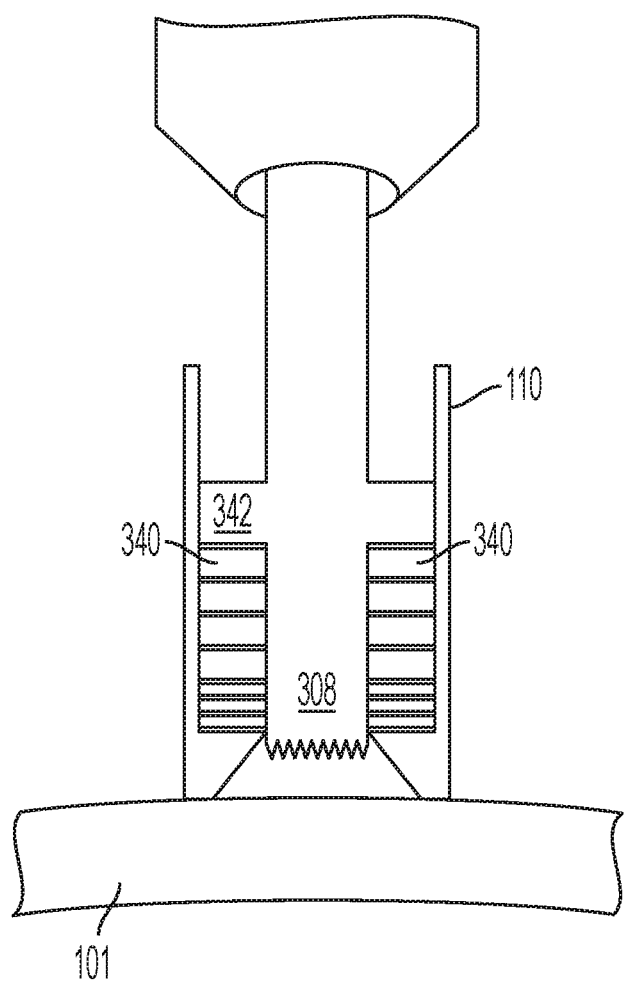
FIG. 10 illustrates one embodiment of a guide-hub with plunge protection.

FIG. 10 illustrates a cross-sectional view of an alternative embodiment of a guide-hub 110 with plunge protection. In such alternative embodiments, plunge protection is provided by a series of drill depth spacers 340 (as opposed to the plunge protection harness 300 described hereinabove). The drill bit 308 includes an expanding stop portion 342 that prevents further drill penetration once the stop portion 342 on the drill bit 308 contacts the topmost drill depth spacer 340. The drill depth spacers 340 are contained in the guide-hub 110 and can be individually removed or realigned to allow the stop portion 342 on the drill bit 308 to continue progressing downward while drilling. The drill depth spacers 340 serve as mechanical stops that prevent plunge once the skull is penetrated by the drill bit 308.

According to some embodiments as shown in FIG. 10, the drill depth spacers 340 can have two different thicknesses, a thicker spacer for initial drilling and a thinner spacer for later drilling as the drill bit approaches the other side of the skull bone and is close to penetrating the skull. In other solutions, the spacers could have the same thickness or multiple (more than two) different thicknesses.

Figure 11A:
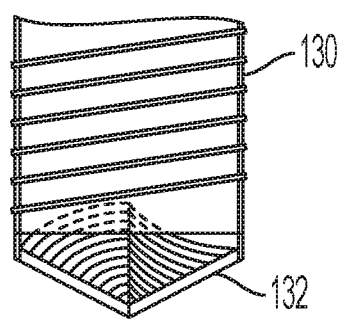
FIGS. 11A-11D illustrate multiple views of one embodiment of a guide-hub.
Figure 11B:
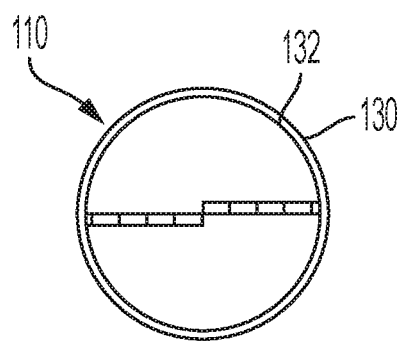
Figure 11C:
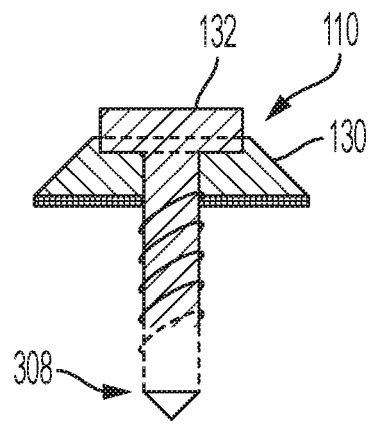
Figure 11D:
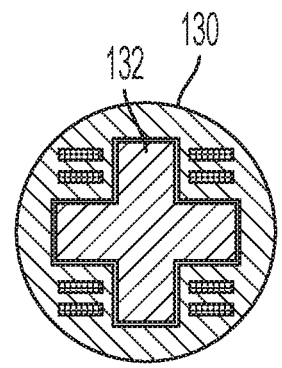

FIGS. 11A, 11B, 11C, and 11D illustrate a guide-hub 110 according to an alternative embodiment. In this embodiment, the guide-hub 110 includes a threaded hollow sheath 130 and an internal cut and drive shaft 132. FIG. 11A illustrates a front view of the threaded hollow sheath 130 and an internal cut and drive shaft 132. FIG. 11B illustrates a bottom view of the guide-hub 110. FIG. 11C illustrates a front view of the guide-hub 110 with the threaded hollow sheath 130 and internal cut and drive shaft 132. FIG. 11D illustrates a top view of the guide-hub 110. The internal cut and drive shaft 132 and the threaded hollow sheath 130 of the guide-hub 110 are drilled into the skull 101 until the threads of the threaded hollow sheath 130 are secured in the skull. The drill continues drilling until the internal cut and drive shaft 132 penetrates the skull. The internal cut and drive shaft 132 is then removed from the guide-hub 110 and a catheter 402 is inserted through the threaded hollow sheath 130 of the guide-hub 110.

Figure 12A:
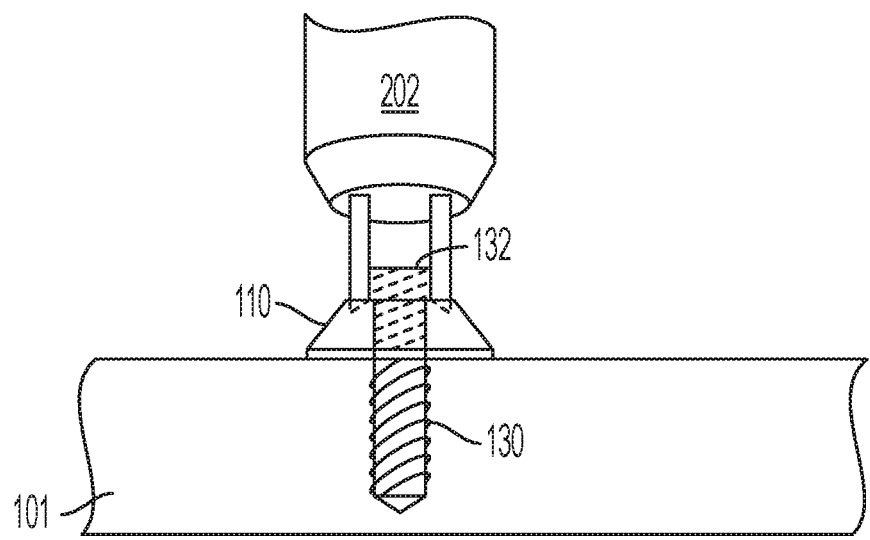
FIGS. 12A-12D illustrate a process for the guide-hub in FIGS. 11A-11D.
Figure 12B:
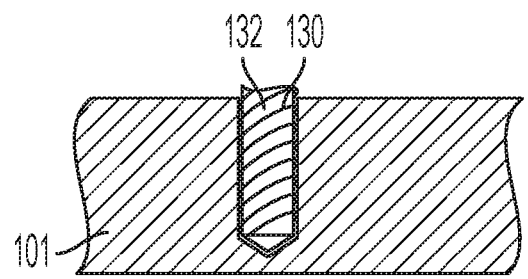
Figure 12C:
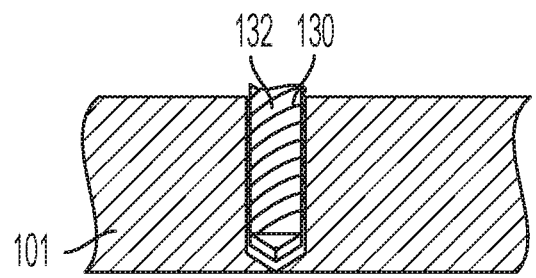
Figure 12D:
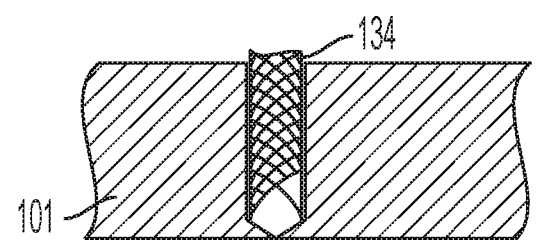

FIGS. 12A, 12B, 12C, and 12D illustrate a process for the guide-hub 110 embodiment described in reference to FIGS. 11A, 11B, 11C, and 11D. As shown in FIG. 12A, a drill 202 drives the guide-hub 110 with the threaded hollow sheath 130 and the internal cut and drive shaft 132 into the skull 101. The threads of the threaded hollow sheath 130 grip into the skull 101. In FIG. 12B, the drilling continues until the internal cut and drive shaft 132 is close to penetrating the skull 101. In FIG. 12C, the internal cut and drive shaft 132 can be removed right before penetrating the skull 101. In FIG. 12D, a cutting piece 134, for example, a sharp wire, is used to break through the last part of the skull, e.g., the bone shelf after drilling. A catheter 402 is then inserted through the hollow portion of the guide-hub 110.

Figure 13:
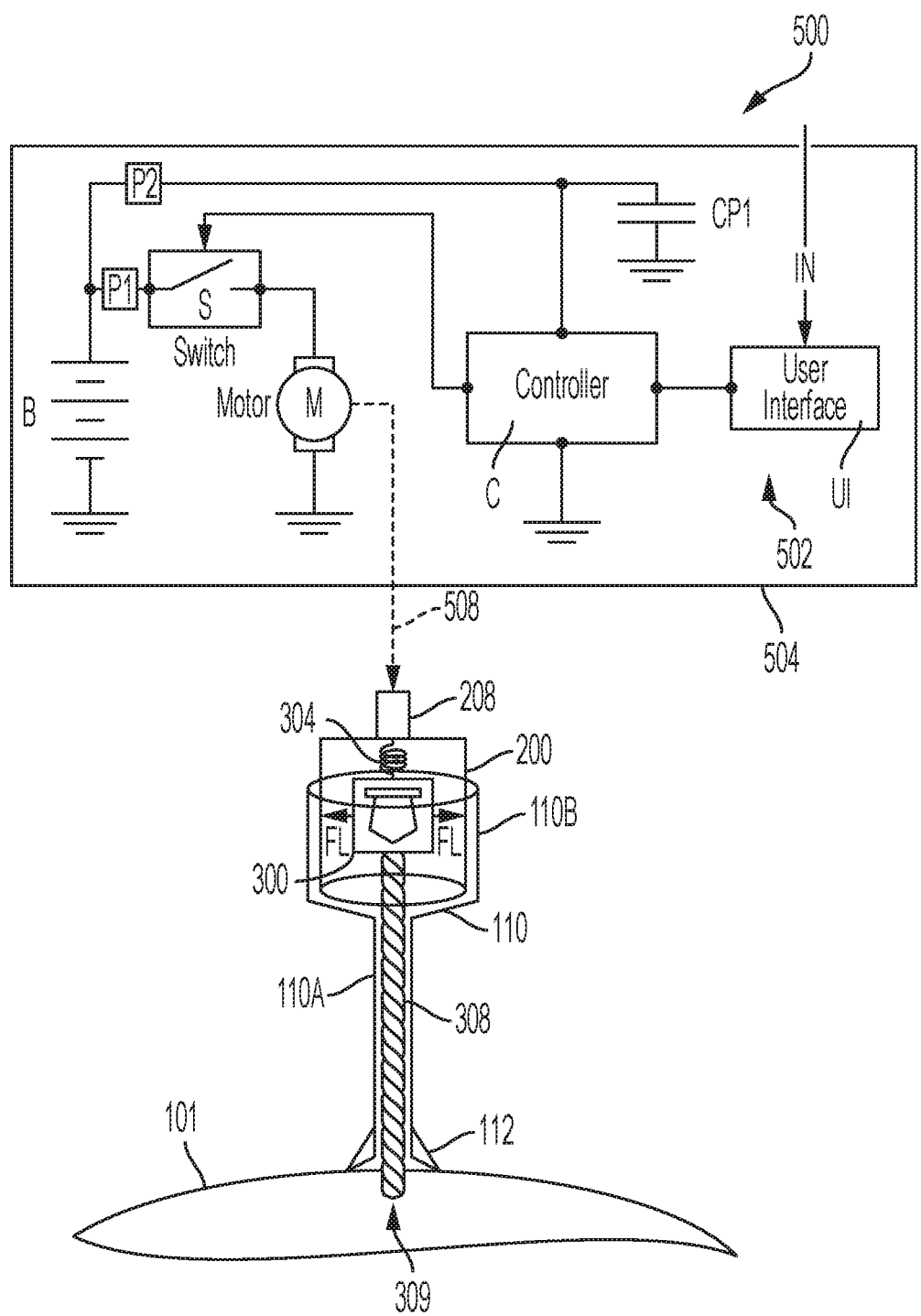
FIG. 13 illustrates one embodiment of a system diagram that includes a control circuit inside a housing and a drilling structure set inside a guide-hub.

FIG. 13 illustrates a system diagram 500 according to various embodiments that includes a control circuit 502 inside a housing 504 and a central drill shell 200 set inside the guide-hub 110. In such embodiments as illustrated in FIG. 13, motor M supplies output shaft drive power 508 to the central drive shaft 208 of the central drill shell 200. Motor M is controlled by a switch S. The switch S is activated to supply power P1 to motor M from a power supply, such as a battery B, as illustrated in FIG. 13. In some embodiments, the switch S is controlled by a controller C that receives user input IN through the user interface UI.

In various embodiments, user input IN may be through a button, switch, or trigger. In some such embodiments, the user interface UI includes the button, switch, or trigger. User input IN may be an on or off signal. In other embodiments, user input IN is a more complex signal that can take on many values to provide variable control. The user interface may include an analog interface circuit. The controller C may be a microcontroller, an analog control circuit, or a digital control circuit. In some embodiments, power circuit P1 or power circuit P2 is included. Power circuit P1 and power circuit P2 provide voltage conversion or regulation. For example, in some embodiments, power circuit P2 converts the voltage supplied by the battery to a first voltage to supply the controller, and power circuit P1 converts the voltage supplied by the battery to a second voltage to supply motor M. In some embodiments, the first voltage and the second voltage are different voltages. In alternative embodiments, the first voltage and the second voltage are the same voltage. Power circuit P1 and power circuit P2 include voltage regulation circuits in some embodiments. In further embodiments, power circuit P1 and power circuit P2 are omitted.

In some embodiments, power regulation capacitor CP1 is included to stabilize the power supply to the controller C or to motor M. In alternative embodiments, power regulation capacitor CP1 is omitted. The battery may be another type of power supply, such as a wired power supply. In some embodiments the battery is rechargeable. In various embodiments, the battery is not rechargeable. In further embodiments, the battery or power supply is provided through a supercapacitor.

According to various embodiments, motor M drives the central drive shaft 208 of the central drill shell 200. Motor M may be controlled to provide variable rotations per minute (RPM) to the central drive shaft 208 in some embodiments. In other embodiments, motor M is controlled to provide variable torque to the central drive shaft 208. As the central drive shaft 208 is driven by motor M, the central drill shell 200 rotates. Inside the central drill shell 200, the plunge protection harness 300 is coupled to the central drill shell 200 such that the plunge protection harness 300 and the drill bit 308 attached to the plunge protection harness 300 also rotate. In such embodiments, the drill bit 308 is driven to rotate and drill into the drilling surface. In some embodiments, the drilling surface is a skull 101 and the drilling is performed as part of a cranial access procedure. For example, one such procedure involves the placement of an EVD for treatment of hydrocephalus.

In various embodiments, the plunge protection harness 300 is coupled to the central drill shell 200 through friction lock FL. In some embodiments, friction lock FL functions by the plunge protection harness 300 expanding outward to press against the inner wall of the central drill shell 200. The inner wall of the central drill shell 200 includes a rough surface, a high friction surface, a ribbed surface, or one or more ridges in various embodiments. In such embodiments, friction lock FL is strengthened by the rough surface, the high friction surface, the ribbed surface, or the one or more ridges. According to various embodiments, the plunge protection harness 300 engages the friction lock FL when a counter force is provided against the drill bit 308 that pushes the plunge protection harness 300 upward. The counter force is present when the drill bit 308 is pressed against a hard surface, such as when the drill bit 308 is pressed against the drilling surface during drilling. As soon as the drilling surface is punctured, the drill bit 308 breaks through the drilling surface and the counter force is removed. In such embodiments, the plunge protection harness 300 disengages friction lock FL and withdraws the drill bit 308 automatically due to the spring 304. The spring 304 is set to a compression state before the plunge protection harness 300 engages friction lock FL and the counter force is applied to the drill bit 308. Thus, once the plunge protection harness 300 disengages friction lock FL due to puncture, the drill bit 308 is automatically withdrawn by the springs 304 restoring force. Note that FIG. 13 represents the plunge protection harness 300 and spring 304 schematically for simplicity of illustration. The details of plunge protection harness 300 and spring 304 are included and describe in reference to the other figures herein, such as in FIG. 14 and FIG. 15, for example. In alternative embodiments, spring 304 may be configured to be set in an extension state instead of a compression state before friction lock FL is engaged.

According to various embodiments, the central drill shell 200 rotates inside the guide-hub 110 during drilling. The guide-hub 110 includes support legs 112 set against the drilling surface. The guide-hub 110 maintains a set drilling angle with the drilling surface due to the support legs 112. In such embodiments, the support legs 112 are rigidly set against the drilling surface and the guide-hub 110 prevents the drill bit 308 from altering the drilling angle during drilling. Thus, the set drilling angle is maintained throughout drilling. In various embodiments, the drilling angle is set such that the drill bit 308 is perpendicular to the drilling surface. In other embodiments, the drilling angle is set so that the drill bit 308 is within 10° of perpendicular, i.e., the drill bit 308 is maintained between 80° and 100° of the drilling surface.

In various embodiments, the drill bit 308 is guided by the lower portion 110A of the guide-hub 110, which has a diameter slightly larger than the drill bit 308. The upper portion 110B of the guide-hub 110 has a larger diameter that is large enough to receive the central drill shell 200 that contains the plunge protection harness 300. According to such embodiments, the lower portion 110A of the guide-hub 110 guides the drill bit 308 and sets the support legs 112 against the drilling surface with a smaller footprint than the upper portion 110B of the guide-hub 110. In such embodiments, the guide hub 110 has a first smaller diameter for the lower portion 110A and a second larger diameter for the upper portion 110B. In some embodiments, the first smaller diameter is less than 4 cm and the second larger diameter is greater than or equal to 4 cm. In particular embodiments, the first smaller diameter is less than or equal to 2 cm and the second larger diameter is between 2 cm and 6 cm. In some embodiments, the second larger diameter may be sized so as to be comfortably gripped in a surgeon's hand. According to a particular embodiment, the first inner diameter is small enough that the support legs 112 may be placed against the skull 101 through an incision in the scalp 103 that is approximately 2 cm.

In various embodiments, the drill bit tip 309 is an abrasive tip. In other embodiments, the drill bit tip 309 is a cutting tip. The drill bit tip 309 is hollow with an abrasive or cutting edge around the diameter of the drill bit tip 309 in some embodiments. In various different embodiments, the drill bit 308 and drill bit tip 309 may include a twist bit, a unibit, a hole saw, a coated abrasive bit, a center drill bit, a core drill, a spade bit, a lip and spur drill bit, an augur bit, a center bit, or a Forstner bit. Particular embodiments without a sharp tip may advantageously reduce complication rates. For example, an abrasive tip, a core drilling tip, or a Forstner bit may provide reduced complication rates.

According to various embodiments, once the drill bit tip 309 punctures the drilling surface and the plunge protection harness 300 retracts the drill bit 308, the central drill shell 200 with the plunge protection harness 300 and drill bit 308 may be removed from the guide-hub 110. Following removal of these pieces, a catheter 402 may be introduced into the area beneath the drilling surface as described further hereinabove in reference to, for example, FIG. 1D and FIG. 2D. The smaller diameter of the lower portion 110A of the guide-hub 110 may serve as a catheter guide 400. In other embodiments, an additional catheter guide 400 may be inserted into the guide-hub 110 to guide the catheter placement. According to various embodiments, the guide-hub 110 guides the catheter placement such that the angle between the drilling surface and the catheter 402 is maintained at the set angle described hereinabove in reference to the drill bit 308 in FIG. 13. In alternative embodiments, the catheter 402 is set to an angle different from the angle of the drill bit 308.

In some alternative embodiments, motor M and the control elements are replaced with a hand crank mechanism controlled by the operator, such as a surgeon. In other alternative embodiments, plunge protection operates without a friction lock FL and includes a torque change sensing element that detects a change in torque corresponding to puncturing the drilling surface. The detected torque change is used to activate the plunge protection harness 300 to withdraw the drill bit 308. In various embodiments, Controller C is configured to detect a voltage change at Motor M that corresponds to puncturing the drilling surface. In particular such embodiments, Controller C deactivates Motor M when puncturing the drilling surface is detected.

Figure 14:
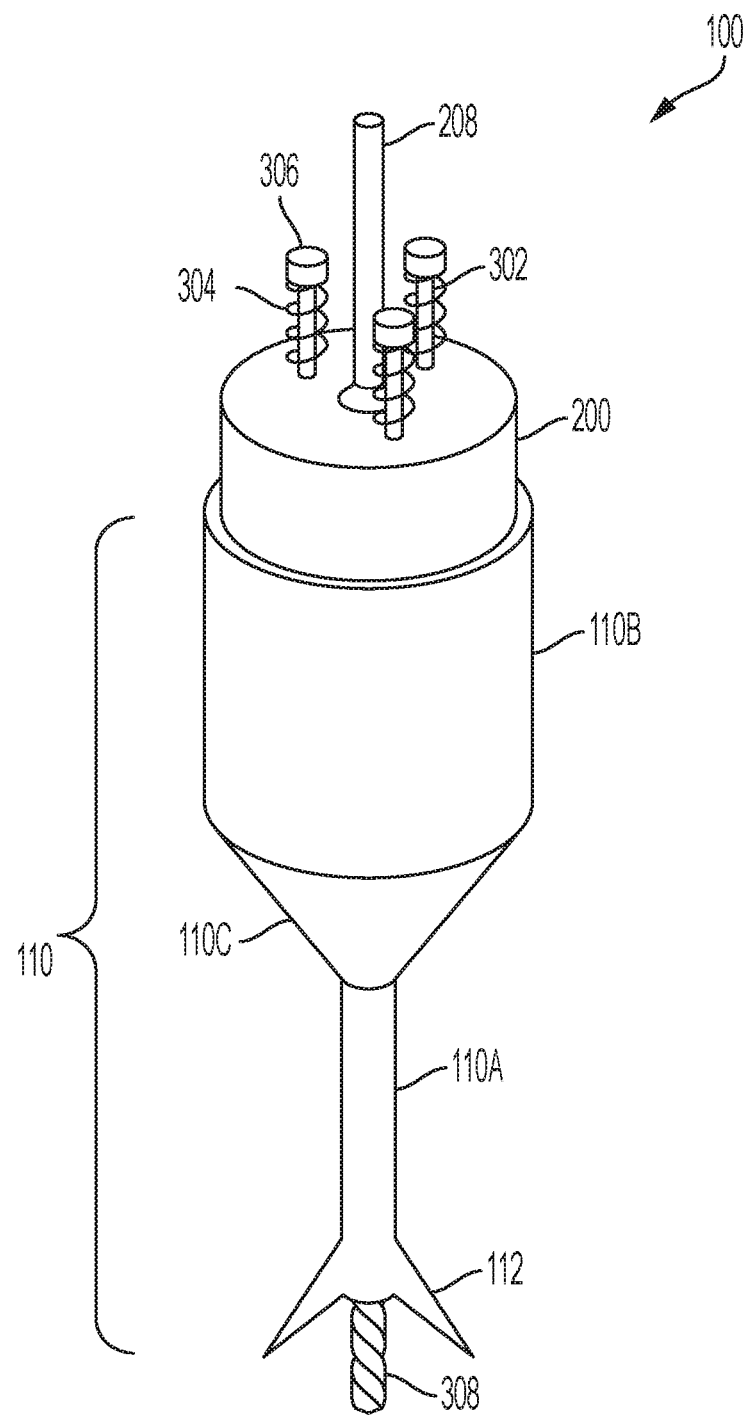
FIG. 14 illustrates a perspective view of one embodiment of a drilling structure.

FIG. 14 illustrates a perspective view of the drilling structure 100 according to various embodiments. The drilling structure 100 includes the central drill shell 200, the guide-hub 110, and the drill bit 308 (which is attached to elements inside the central drill shell 200 as described hereinbelow in reference to FIG. 15). As described in detail in reference to FIG. 13, the central drill shell 200 rotates inside the guide-hub 110 due to a driving force applied by a motor (not shown in FIG. 14) to the central drive shaft 208 at the top-most portion of the central drill shell 200. According to some embodiments, the central drill shell 200 includes springs 304 as part of the plunge protection harness 300 (described in reference to FIG. 13 hereinabove and in more detail in reference to FIG. 15 hereinbelow). In such embodiments, the springs 304 are set between the top surface of the central drill shell 200 and stoppers 306 on support shafts 302 (support shafts 302 extend inside the central drill shell 200). The support shafts 302 attach to the joint shoulder 310 (illustrated and described hereinbelow in reference to FIG. 15) and, together with the springs 304 and joint arms 320 (illustrated and described hereinbelow in reference to FIG. 15), form the plunge protection harness 300. The springs 304 illustrated in FIG. 14 are compressed before friction lock FL is engaged. In such embodiments, the springs 304 restoring force after puncture (when the counter force on the drill bit 308 is removed) is due to compression of the springs 304. In alternative embodiments, the springs 304 may be configured to be set in an extension state instead of a compression state before friction lock FL is engaged. In some such embodiments, the springs 304 would be arranged inside central drill shell 200 (not shown), underneath the top surface instead of on top of the top surface (as shown) of central drill shell 200.

In some embodiments, the guide-hub 110 includes a tapered portion 110C from the lower portion 110A of the guide-hub 110 to the upper portion 110B of the guide-hub 110 as illustrated. In other embodiments, the tapered portion 110C is omitted and the transition between the lower portion 110A and the upper portion 110B is a flat portion perpendicular to the outer cylindrical surfaces (not shown). In various embodiments, the guide-hub 110 includes three support legs 112 at the bottom, of which only two support legs 112 are visible in the perspective view of FIG. 14 (the third is hidden behind the drill bit 308). In other embodiments, four or five support legs 112 are included in the guide-hub 110. In still further embodiments, more than five support legs 112 are included. In a particular alternative embodiment, only two support legs 112 are included. In this particular alternative embodiment, the angle setting functionally for the drill bit 308 and the catheter 402 placement is limited.

Figure 15:
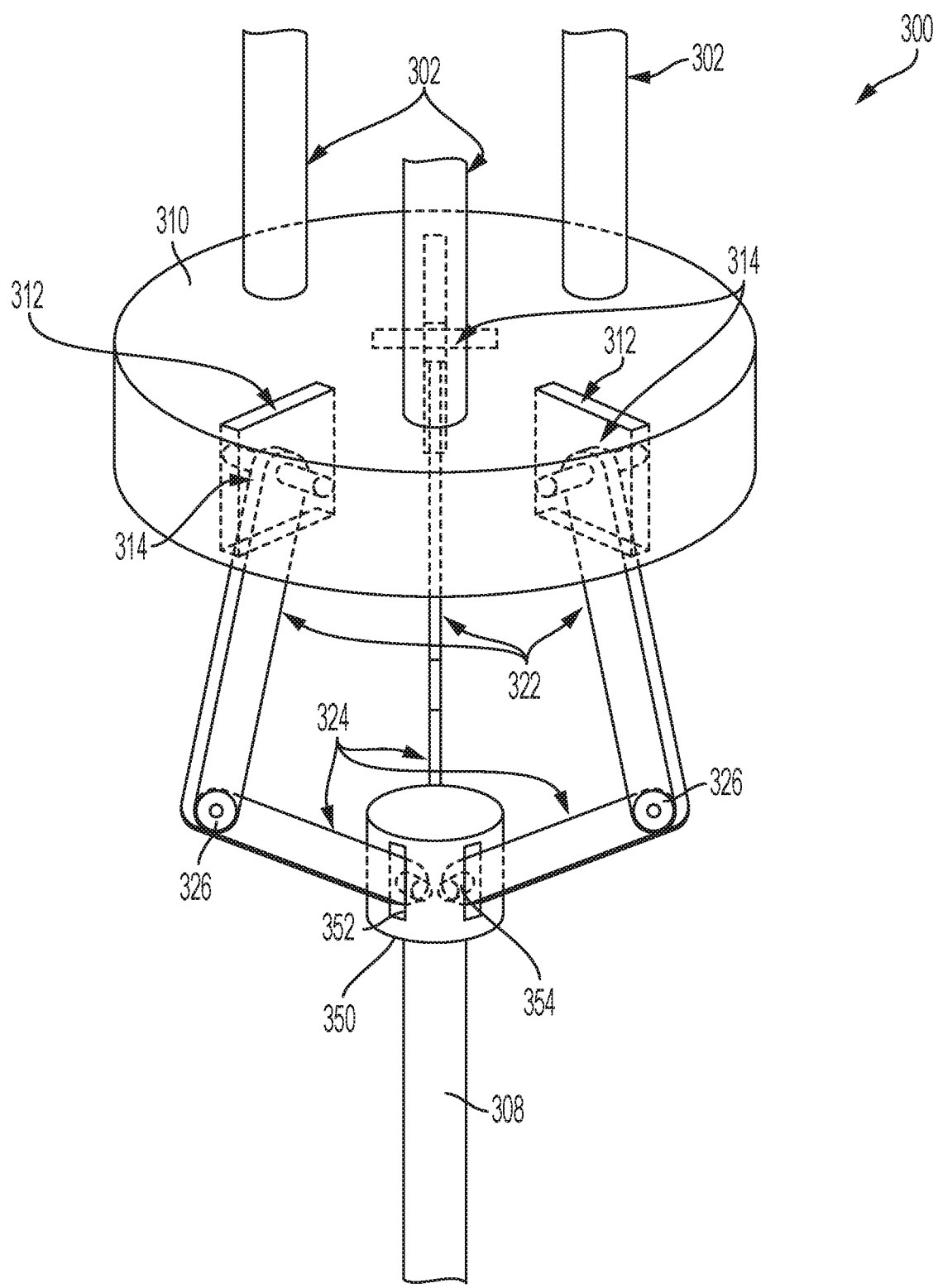
FIG. 15 illustrates a perspective view of one embodiment of a plunge protection harness.

FIG. 15 illustrates a cut-away view showing portions of the plunge protection harness 300 included inside the central drilling shell 200 according to various embodiments as described hereinabove in reference to FIG. 13 and FIG. 14.

In such embodiments, the support shafts 302 are connected to and support the joint shoulder 310. The support shafts 302 extend downward from outside the central drill shell 200, where the support shafts 302 are coupled to the central drill shell 200 through the springs 304, as described hereinabove in reference to FIG. 14. The joint shoulder 310 supports the joint arms 320, drill bit coupling 350, and drill bit 308.

According to various embodiments, the joint shoulder 310 includes upper joint arm slots 312 where the joint arms 320 hang down from the joint shoulder 310 and each include an upper joint arm 322 and a lower joint arm 324 coupled through a joint hinge 326. The upper joint arms 322 are connected to joint shoulder hinges 314 inside the upper joint arm slots 312 of the joint shoulder 310. The lower joint arms 324 are coupled to the drill bit coupling 350 through coupling hinges 354 inside lower joint arm slots 352 of the drill bit coupling 350.

In various embodiments, when a counter force is applied to the drill bit 308, such as during drilling, the counter force pushes the drill bit 308 up and causes the joint hinges 326 to rotate inward as the joint arms 320 push outward. The joint arms 320 contact the inner wall (not shown) of the central drill shell 200 and form friction lock FL with the inner wall as described hereinabove in reference to FIG. 13 and FIG. 14. Once the joint arms 320 contact the inner wall of the central drill shell 200, the drill bit 308 stops moving upward and drilling is performed while pressure is maintained. When the central drill shell 200 rotates due to a driving force from a motor (described hereinabove in reference to the other figures), the joint arms 320 rotate with the central drill shell 200 due to friction lock FL, and as the joint arms 320 rotate, the drill bit coupling 350 and the drill bit 308 rotate. Once puncture occurs, the counter force is removed from the drill bit 308, the joint arms 320 disengage friction lock FL, and the spring 304 (described hereinabove in reference to FIG. 13 and FIG. 14), which includes three springs in FIG. 13 and FIG. 14 but may include one or more springs, withdraws the plunge protection harness 300 automatically. Thus, the drill bit 308 is pulled back away from the hole in the drilling surface (see, FIG. 13). In some embodiments, the drill bit 308 is withdrawn out of the hole in the drilling surface (see, FIG. 13) entirely. In other embodiments, the drill bit 308 is prevented from advancing further into the hole in the drilling surface (see, FIG. 13).

In some embodiments, three joint arms 320 are included as illustrated in FIG. 15. In other embodiments, four or five joint arms 320 are included. In still further embodiments, any number of joint arms 320 are included, such as only two or more than five. The joint arms 320 are illustrated with single members for the upper joint arm 322 and the lower joint arm 324 in accordance with an embodiment. In other embodiments, the lower joint arm 324 may include two members, one on each side of the upper joint arm 322 at the joint hinge 326. In still other embodiments, the upper joint arm 322 may include two members, one on each side of the lower joint arm 324 at the joint hinge 326. According to some embodiments, any type of hinge or joint may be used at the joint hinge 326. According to some embodiments, any type of hinge or joint may be used at the joint shoulder hinge 314 or the coupling hinge 354.

Figure 16B:
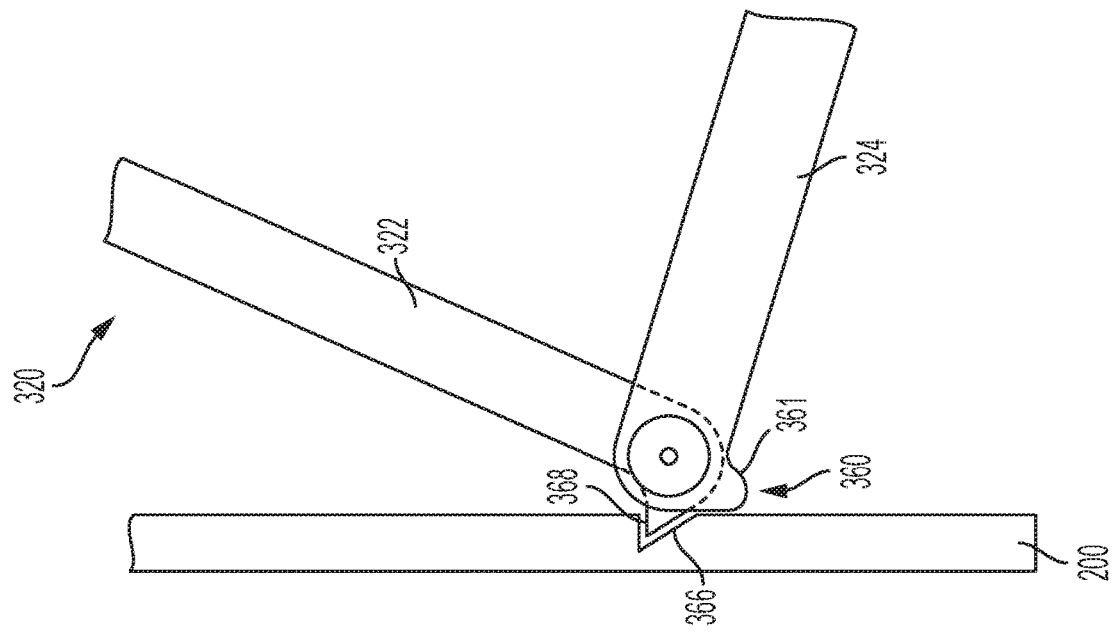
FIGS. 16A and 16B illustrates magnified views of a joint arm interface.
Figure 16A:
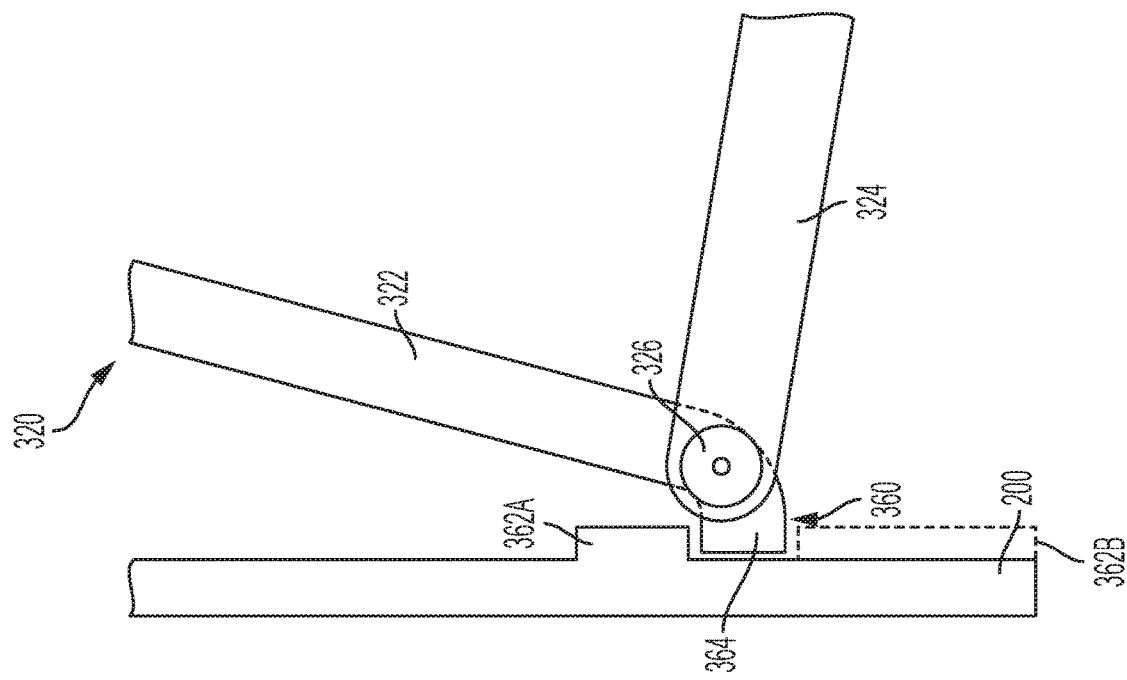

FIGS. 16A and 16B illustrate further embodiments for of the joint arms 320 for friction lock FL. As described in reference to FIG. 13, the inner wall of the central drill shell 200 may include a rough surface, a high friction surface, a ribbed surface, or one or more ridges in various embodiments. In further embodiments, a mechanical connection is included between the central drill shell 200 and the joint arms 320. The mechanical connection implements friction lock FL and provides further robustness of the lock during drilling where the mechanical connection is relied upon beyond a friction only based connection. FIGS. 16A and 16B illustrate zoom-in views of a joint arm 320 interface with the central drill shell 200 according to two example embodiments. As described in reference to the other figures, such as FIG. 15 above, there may be multiple joint arms 320, but only a single joint arm 320 is illustrated in each of FIGS. 16A and 16B in the zoom-in views.

In FIG. 16A, a mechanical connection 360 is between the joint arm 320 and the central drill shell 200. In such embodiments, the upper joint arm 322 includes a joint hook 364 that catches on a ridge 362A on the inside surface of central drill shell 200. During drilling when the joint arms 320 are extended and in contact with the central drill shell 200, as described further hereinabove in reference to the other figures (such as FIGS. 13, 14, and 15), the joint hook 364 locks in place with the ridge 362A to form mechanical connection 360. In such embodiments, mechanical connection 360 implements friction lock FL and includes the mechanical connection in addition to the friction-based connection.

In various embodiments, the central drill shell 200 may include protrusion 362B (shown in broken lines), such that protrusion 362B and ridge 362A form an indentation between them in central drill shell 200 where the joint hook 364 engages when the counter force is transferred into the joint arms 320 to cause them to expand, as described hereinabove in reference to the other figures (such as FIGS. 13, 14, and 15). In some embodiments, there may be multiple of the ridges 362A on the inside surface of central drill shell 200, but FIG. 16A illustrates only one of ridge 362A for simplicity of illustration.

In FIG. 16B, a mechanical connection 360 is between the joint arm 320 and the central drill shell 200 as similarly described in reference to mechanical connection 360 in FIG. 16A. Mechanical connection 360 is formed by an angled joint hook 368 that catches on an angled indentation 366 in central drill shell 200. In some embodiments, there may be multiple of the angled indentations 366 on the inside surface of central drill shell 200, but FIG. 16B illustrates only one of angled indentation 366 for simplicity of illustration.

In some alternative embodiments, the lower joint arm 324 may also include a disengaging bump 361, which functions to push angled the joint hook 368 out of the angled indentation 366 once the counter force is removed and the lower joint arm 324 begins to rotate downward.

One element or feature included in various embodiments as contemplated here that is not illustrated in the figures is position tracking for further improved catheter placement accuracy. In a first version with position tracking, the guide-hub 110 and drilling structure 100 may integrate with an augmented reality system that will overlay the patient's brain scan and guide drilling or catheter placement. In such solutions, the guide-hub 110 may include markers or other indicia for use with the augmented reality system to calibrate and align the drilling and catheter insertion. The augmented reality system could also be implemented as a virtual reality system. In a second version with position tracking, the guide-hub 110 may include a position sensor system that calculates the position of the guide-hub 110 and the target position and alignment. The guide-hub 110 would include an indicator, such as an LED light or array, that indicates to the neurosurgeon when the guide-hub 110 is positioned correctly for drilling and catheter insertion. The position sensor system may include accelerometers or gyroscopes, infrared position tracking, EMF based triangulation, or other position tracking systems. In this solution, the position tracking and calculation could be done automatically without the neurosurgeon's interaction and the system could be used to indicate to the neurosurgeon the correct position of the guide-hub before drilling.

The various embodiments are described at a high level. It is envisioned that various embodiments would be combined in part or in whole for different embodiments. Further, various modifications, additions, or subtractions might be made within the scope of this disclosure as will be readily appreciated by those of skill in the art. The initial description is presented in reference to a procedure for placing EVDs, however other procedures for accessing the brain are contemplated and the solutions described herein are intended for use with additional procedures.

What is claimed is:

1. A cranial access drilling system comprising:
   a guide-hub configured to be placed against a cranial drilling surface, to maintain a fixed angle with the cranial drilling surface, and to remain stationary during drilling along a drilling trajectory;
   a drilling insert comprising a drill bit and configured to be mechanically coupled to a motor,
      wherein the drilling insert is configured to be inserted into the guide-hub and rotated within the guide-hub along with the drill bit by the motor, and
      wherein the drilling insert is configured to automatically prevent further drilling in response to detecting that the drill bit punctures the cranial drilling surface; and
   a catheter guide configured to be inserted into the guide-hub, the guide-hub being further configured to guide a catheter along a catheter trajectory.

2. The cranial access drilling system of claim 1, wherein the drilling insert comprises a plunge protection harness, and wherein the plunge protection harness comprises a hinge system configured to engage a friction lock during drilling and to disengage the friction lock and withdraw the drill bit automatically when the drill bit punctures the cranial drilling surface.

3. The cranial access drilling system of claim 2, wherein the hinge system comprises at least three displaceable arms surrounding and supporting the drill bit in the plunge protection harness and configured to form the friction lock, each of the at least three displaceable arms being connected to the drill bit at a proximal end and to the plunge protection harness at a distal end.

4. The cranial access drilling system of claim 2, wherein the plunge protection harness comprises spring configured to facilitate automatic drill bit retraction to automatically prevent the further drilling, the springs being configured to rotate along with the drilling insert and the drill bit.

5. The cranial access drilling system of claim 1, wherein the guide-hub comprises contact feet, and wherein the contact feet further comprise feet extensions,
   wherein the contact feet are connected to the feet extensions by a joint, and
   wherein the joint is configured to rotate towards the guide-hub and the feet extensions are configured to rotate in conjunction with the joint.

6. The cranial access drilling system of claim 1, further comprising:
   a controller coupled to a plunge protection harness of the drilling insert and configured to deactivate the motor when puncturing of the cranial drilling surface is detected, the plunge protection harness being configured to detect when the drill bit punctures the cranial drilling surface to prevent further plunge using an electrical parametric change that corresponds to puncturing the cranial drilling surface.

7. The cranial access drilling system of claim 1, wherein the catheter guide is further configured to be inserted into the guide-hub after drilling.

8. The cranial access drilling system of claim 7, wherein the drilling insert is further configured to be removed from the guide-hub after drilling so that when the catheter guide is inserted into the guide-hub, the catheter guide replaces the drilling insert in the guide-hub.

9. The cranial access drilling system of claim 7, wherein the catheter guide includes a depth gauge configured to display accurate catheter placement depth.

10. The cranial access drilling system of claim 7, wherein the catheter guide is of substantially similar height as the guide-hub.

11. The cranial access drilling system of claim 1, wherein the catheter guide is integrated into the guide-hub.

12. The cranial access drilling system of claim 1, wherein the catheter trajectory is the same as the drilling trajectory.

13. The cranial access drilling system of claim 1, wherein the catheter guide is further configured to set the catheter trajectory at a predetermined angle relative to and different from the drilling trajectory.

14. The cranial access drilling system of claim 1, further comprising ball bearings disposed within the guide-hub between the drilling insert and the guide-hub, the ball bearings being configured to allow rotation of the drilling insert while the guide-hub remains stationary.

15. A medical tool comprising:
   a cranial access drill comprising:
      a motor;
      a guide-hub configured to be placed against a cranial drilling surface and to maintain a fixed angle with the cranial drilling surface;
      a drill bit;
      a controller,
         wherein the drill bit is configured to be inserted into the guide-hub, and
         wherein the controller is configured to detect an electrical parametric change at the motor that corresponds to puncturing the cranial drilling surface, and wherein the controller is configured to deactivate the motor when puncturing the cranial drilling surface is detected; and
   a catheter guide configured to be inserted into the guide-hub, the guide-hub being further configured to guide a catheter along a catheter trajectory.

16. The medical tool of claim 15, wherein the guide-hub comprises contact feet, and wherein the contact feet further comprise feet extensions,
   wherein the contact feet are connected to the feet extensions by a joint, and
   wherein the joint is configured to rotate towards the guide-hub and the feet extensions are configured to rotate in conjunction with the joint.

17. The medical tool of claim 15,
   wherein the drill bit is further configured to be removed from the guide-hub after drilling, and
   wherein the catheter guide is further configured to be inserted into the guide-hub after removing the drill bit so that when the catheter guide is inserted into the guide-hub, the catheter guide replaces the drill bit in the guide-hub.

18. The medical tool of claim 15, wherein the catheter guide is integrated into the guide-hub.

19. A cranial access drilling system comprising:
- a guide-hub configured to be placed against a cranial drilling surface, to maintain a fixed angle with the cranial drilling surface, and to remain stationary during drilling along a drilling trajectory,
  - wherein the guide-hub comprises contact feet comprising feet extensions, the contact feet being connected to the feet extensions by a joint, and
  - wherein the joint is configured to rotate towards the guide-hub,
  - wherein the feet extensions are configured to rotate in conjunction with the joint;
- a drilling insert comprising a drill bit and a plunge protection harness, the drilling insert being configured to be mechanically coupled to a motor, to be inserted into the guide-hub and rotated within the guide-hub along with the drill bit by the motor, and to automatically prevent further drilling in response to detecting that the drill bit punctures the cranial drilling surface,
  - wherein the plunge protection harness comprises a hinge system configured to engage a friction lock during drilling and to disengage the friction lock and withdraw the drill bit automatically when the drill bit punctures the cranial drilling surface, and
  - wherein the hinge system comprises at least three displaceable arms surrounding and supporting the drill bit in the plunge protection harness and configured to form the friction lock, each of the at least three displaceable arms being connected to the drill bit at a proximal end and to the plunge protection harness at a distal end; and
- a catheter guide configured to be inserted into the guide-hub, the guide-hub being further configured to guide a catheter along a catheter trajectory.

20. The cranial access drilling system of claim 19,
- wherein the drilling insert is further configured to be removed from the guide-hub after drilling, and
- wherein the catheter guide is further configured to be inserted into the guide-hub after removing the drilling insert so that when the catheter guide is inserted into the guide-hub, the catheter guide replaces the drilling insert in the guide-hub.

\* \* \* \* \*

UNITED STATES PATENT AND TRADEMARK OFFICE
CERTIFICATE OF CORRECTION

PATENT NO. : 11,684,376 B2
APPLICATION NO. : 17/061040
DATED : June 27, 2023
INVENTOR(S) : Ayer et al.

It is certified that error appears in the above-identified patent and that said Letters Patent is hereby corrected as shown below:

In the Claims

In Column 15, in Claim 4, Line 50, delete "spring" and insert -- springs --.

Signed and Sealed this
Twelfth Day of September, 2023

Katherine Kelly Vidal
*Director of the United States Patent and Trademark Office*